United States Patent [19]

Levine et al.

[11] Patent Number: 4,908,387
[45] Date of Patent: Mar. 13, 1990

[54] USE OF BETA$_2$ ANTAGONISTS IN THE TREATMENT OF INFLAMMATORY DISEASES IN IN PARTICULAR RHEUMATOID ARTHRITIS

[75] Inventors: Jon D. Levine; Allan I. Basebaum, both of San Francisco, Calif.

[73] Assignee: The Regents of the University of California, Berkeley, Calif.

[21] Appl. No.: 203,355

[22] Filed: Jun. 6, 1988

[51] Int. Cl.$^4$ .......................................... A61K 31/135
[52] U.S. Cl. .................................................... 514/653
[58] Field of Search ......................................... 514/653

[56] References Cited

PUBLICATIONS

Chem. Abst., vol. 102 (1985)–197713p.
Vyden et al., "The Effect of Propranolol on Peripheral Hemodynamics in Rheumatoid Arthritis," Arthritis and Rheumatism (1971) 14:420.
Levine et al., "Contribution of Sensory Afferents and Sympathetic Efferents to Joint Injury in Experimental Arthritis," J. Neurosci. (1986) 6:3423–3429.
Levine et al., "Clinical Response to Regional Intravenous Guanethidine in Patients with Rheumatoid Arthritis," J. Rheumatol. (1986) 13:1040–1043.
Kaplan et al., "Propranolol and the Treatment of Rheumatoid Arthritis," Arthritis and Rheumatism (1980) 23:253–255.
Levine et al., "Hypothesis: The Nervous System May Contribute to the Pathophysiology of Rheumatoid Arthritis," J. Rheumatol. (1985) 12:406–411.
"A Comprehensive Report on the Pharmacology and Toxicology of Butoxamine (B.W. 64-9)," Burroughs Wellcome & Co. (1965).
"A Supplementary Report on the Pharmacology and Toxicology of Butoxamine (B.W. 64-9)," Burroughs Wellcome & Co. (1966).

Primary Examiner—Stanley J. Friedman
Attorney, Agent, or Firm—Townsend and Townsend

[57] ABSTRACT

A method of treating inflammation and joint deterioration in mammals which comprises administering a therapeutically effective amount of a selective beta$_2$ adrenergic receptor antagonist. The method is particularly useful for the treatment of rheumatoid arthritis in humans.

23 Claims, No Drawings

USE OF BETA₂ ANTAGONISTS IN THE TREATMENT OF INFLAMMATORY DISEASES, IN PARTICULAR, RHEUMATOID ARTHRITIS

BACKGROUND OF THE INVENTION

This invention was made with Government support under Grant Nos. AM32634, NS21642, DE05369, and NS14627 awarded by the Department of Health and Human Services. The Government has certain rights in this invention.

FIELD OF THE INVENTION

This invention concerns the use of selective beta₂ antagonists as active agents in the treatment of inflammatory diseases, particularly rheumatoid arthritis.

RELATED DISCLOSURES

Inflammatory diseases, in particular rheumatoid arthritis, have been treated with a wide variety of compounds representing many different structural and pharmacologic classes, including, for example, aspirin and related compounds, non-steroidal anti inflammatory agents (NSAIDS) such as indomethacin, naproxen, ibuprofen and the like, corticosteroids, immunosuppressive, opiates, antimalarials such as hydroxychloroquine and chloroquine, cytotoxics such as cyclophosphamide, chlorambucil and azathioprine, penicillamine and its derivatives, and heavy metals such as the gold salts. No representative of any of these classes is regarded as ideal. Moreover, of these, only penicillamine, some gold compounds and possibly the corticosteroids in high doses have been shown to significantly suppress the progress of rheumatoid arthritis disease (disease modification). The magnitude of thee effects, however, are small, and decrease with time. Further, these compounds possess such severe toxicities that they are reserved for patients whose disease progresses rapidly inspite of treatment with less toxic agents. Finally, all of the drugs available for treating inflammatory disease, whether for symptomatic relief or disease modification, possess side effects which make drug tolerance a serious problem for many patients. The available therapies are especially poorly tolerated by aged individuals, in whom inflammatory diseases are particularly prevalent and debilitating.

None of the drugs presently available for treating inflammatory disorders are known to act via the nervous system. However, researchers have recently noted an apparent contribution of the sympathetic nervous system to the proliferation of inflammatory conditions and processes. It has been reported that dogs chronically maintained on beta adrenergic agonists develop a rheumatoid arthritis like syndrome [Vyden et al. *Arthritis Rheum.* 14, 420, (1971)]. The inventors of the present invention, in conjunction with colleagues, have reported on studies showing that sympathectomy markedly attenuates the signs of inflammation and severity of joint injury in rats with experimentally induced arthritis and that intracerebroventricular administration of morphine, which is known to decrease sympathetic tone, decreases arthritic severity [Levine et al., *J.Neurosci.* 6, 3423-3429 (1986)]. The inventors have also reported that regional sympathetic blockade with guanethidine reduces pain and increases pinch strength in patients with active rheumatoid arthritis [Levine et al., *J. Rheumatol.*, 13, 1040-1043 (1986)]. Finally, propranolol, a beta adrenergic blocker, has been shown, in very high doses that produce significant toxicity, to decrease signs and symptoms of inflammation, in patients with active rheumatoid arthritis; suppression of joint deterioration was not shown. [Kaplan et al., *Arthritis Rheum.* 23, 253-255 (1980)].

However, none of these approaches provides a therapeutically acceptable method of treating inflammatory diseases. Adrenergic neuron blocking agents such as guanethidine and reserpine, produce sympathetic neural block by depleting neuronal stores of catecholamines Thus, in contrast to adrenergic receptor blocking agents, responses mediated by alpha- and beta-adrenergic receptors are suppressed about equally, providing strong cardiovascular effects including decreased arterial pressure, decreased cardiac output, and postural hypotension. For these reasons, sympathectomy via systemic drug administration is not therapeutically feasible. Propranolol is a non-selective beta adrenergic blocking agent, or antagonist, that is used widely for the treatment of hypertension, the prevention of angina pectoris and the control of cardiac arrhythmias. Its activity on the cardiovascular system, as well as serious toxicities associated with chronic administration at high (anti-inflammatory) doses, make its use inappropriate for inflammatory disorders.

Thus, there is a need for a new method of treating chronic severe inflammatory diseases which substantially avoids the toxicities and tolerance problems associated with currently available therapies and the unwanted cardiovascular effects of the nonselective neural and beta-adrenergic blocking agents.

SUMMARY OF THE INVENTION

Accordingly, it is an object of this invention to provide a method of treating inflammatory disorders in mammals which comprises administering a therapeutically effective amount of a selective beta₂ antagonist to a subject in need of such treatment. Surprisingly, it has now been discovered that administration of a selective beta₂ antagonist provides significant inhibitory effect on the signs and progress of diseases characterized by inflammation and progressive deterioration of joints and tissues of the mammalian musculoskeletal system. Accordingly, it is a further object of this invention to provide a method of treating a disorder in a mammal characterized by the presence of progressive joint deterioration, which method comprises administering a therapeutically effective amount of a selective beta₂ antagonist to a subject in need of such treatment.

DETAILED DESCRIPTION AND PREFERRED EMBODIMENTS OF THE INVENTION

Definitions

The following definitions are set forth to illustrate and define the meaning and scope of the various terms used to describe the invention.

As used herein, the term "selective beta₂ antagonist" means an active agent having beta adrenergic blocking activity which is selective for beta₂-adrenergic receptors. Beta₂-adrenergic receptors are found primarily in skeletal and smooth muscle, bone, cartilage, connective tissue, the intestines, lungs, bronchial glands and liver. Beta₁-adrenergic receptors are found primarily in the heart, blood vessels and adipose tissue. For use in this invention, an active agent having beta adrenergic blocking activity should preferably exhibit at least 10-fold greater potency in binding to beta₂- than to beta1-adrenergic receptors, i.e. have a beta$_2$/beta$_1$ selectivity ratio of at least 10. More preferably, the selective beta$_2$ antagonist will have a beta$_2$/beta$_1$ selectivity ratio of at least 50. The affinity of various active agents for beta$_1$ and beta$_2$ receptors can be determined by evaluating tissues containing a majority of beta$_2$ receptors (e.g., rabbit ciliary process, rat liver, cat choroid plexus or lung), tissues containing a majority of beta$_1$ receptors (e.g., cat and guinea pig heart), and tissues containing a mixture (e.g. guinea pig trachea). The methods of determining relative binding selectivities for these different types of tissues are extensively disclosed in O'Donnell and Wanstall, *Naunyn-Schmiedeberg's Arch.Pharmaco.*, 308, 183–190 (1979), Nathanson, *Science.* 204, 843–844 (1979), Nathanson, *Life Sciences*, 26, 1793–1799 (1980), Minneman et al., *Mol.Pharmacol.*, 15, 21–33 (1979a), and Minneman et al., *Journal of Pharmacology and Experimental Therapeutics*, 211, 502–508 (1979), all of which are herein incorporated by reference.

A significant number of compounds having selective beta$_2$ antagonist activity suitable for use in this invention are known. These include, but are not limited to, butoxamine, ICI 118,551, H35/25, prenalterol, various 4- and 5-[2-hydroxy-3-(isopropylamino)propoxy]benzimidazoles, 1-(t-butyl-amino-3-ol-2-propyl)oximino-9 fluorene and various 2-(alpha-hydroxyarylmethyl)-3,3-dimethylaziridines. Methods of synthesis, beta$_2$/beta$_1$ selectivity ratios and various biologic and pharmacologic properties of these compounds are known, and reported in for example, *J. Pharm. Pharmacol.*, 1988, 32(9), 659–660; *J. Med. Chem.*, 22(2), 210–214 (1979); *J. Med. Chem.*, 21(1), 68–72 (1978); *J. Med. Chem.*. 20(12), 1657–62 (1977); and *Br. J. Pharmacol.*. 60(3), 357–362 (1977), all of which are herein incorporated by reference.

The preferred beta$_2$ antagonists for use in this invention are butoxamine, H35/25, and ICI 118,551. The chemical name for butoxamine is DL-erythro-α-(2,5-dimethoxyphenyl)-β-t-butyl aminopropanol hydrochloride. It is available from Burroughs Wellcome Co., Research Triangle Park, N.C. Determination of the Beta$_2$ selectivity of butoxamine is reported in O'Donnell and Wanstall, *Naunyn-Schmiedeberg's Arch.Pharmaco.*, 308, 183–190 (1979), incorporated herein by reference, which reports a beta$_2$/beta$_1$ selectivity ratio of at least 17. The chemical name of ICI 118,551 is erythro-D,L-1(methylinden-4-yloxy)-3-isopropylaminobutan-2-ol. Its synthesis and pharmacologic properties are described in EPO patent specification No. 3664 published 1979, which is incorporated herein by reference. ICI 118,551 has a beta$_2$/beta$_1$ selectivity ratio of at least 50, as determined and reported in *Life Sciences*, 27,671 (1980) and Bilsky et al., *J.Cardiovasc.Pharmacol.*, 5, 430–437 (1983), both of which are incorporated herein by reference. The chemical name for H35/25 is 1-(4'-methylphenyl)-b 2,2-1 -isopropylaminopropanol.

As used herein, the term "treatment" or "treating" means any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of clinical symptoms of the disease.

Utility and Administration

Selective beta$_2$ antagonists have been shown in standard laboratory tests to be useful in treating chronic inflammatory diseases, including models of rheumatoid arthritis, in mammals. Accordingly, the selective beta$_2$ antagonists, and pharmaceutical compositions containing them, may be used in treating inflammatory conditions with a sympathetic nervous system component, particularly rheumatoid arthritis, by administering a therapeutically effective amount of the selective beta$_2$ antagonist to a mammal in need thereof. The clinical observation that patients who have had a stroke, or cerebrovascular accident, do not develop gout, osteoarthritis and other forms of inflammatory arthritis (including rheumatoid arthritis) suggests that many forms of arthritis and chronic inflammatory disease may be mediated by the sympathetic nervous system and subject to treatment with beta$_2$ antagonists.

Anti-inflammatory activity can be determined by several standard laboratory procedures which are well established animal models of inflammatory disease in mammals. These include, for example, the carageenan-induced hindpaw edema model in rats of Winter et al., *Proc.Soc.Exp.Biol.Med.*. 111, 544–547 1962, the cotton pellet-induced granuloma formation model in rats of Meier et al., *Exoerientia* 6, 469–471, 1950, the adjuvant-induced arthritis model in the rat of C. M. Pearson in *Proc.Soc.Exp.Biol.Med.*, 91, 95–101, 1956, the croton oil-inflamed ear model in rats of Tonelli et al., *Endocrinology* 77, 625–634, 1965, the carageenan-induced plural effusion model in the rat of Ackerman et al., *J.Pharm.Exp.Ther.* 215, 588, 1980, and the radiologic evaluation of the adjuvant-induced arthritis model in rats of Ackerman et al., *Arthritis Rheum.* 22, 1365–1374, 1979. The latter method is described in detail in Examples 1 and 2 herein below.

An important aspect of this invention is the discovery that selective beta$_2$ antagonists are potent inhibitors of joint deterioration in arthritic disease. The potency of beta$_2$ antagonists in the suppression of joint deterioration can be determined by the method described in Example 1 hereinbelow. Correlation of results obtained by this method with results obtained from histological section of arthritic joints and periarticular tissues is established. (See Ackerman et al., *Arthritis Rheum.*, 22, 1365–1374, 1979).

Accordingly, the methods of this invention possess utility in the treatment of a large number of disease states in which joint deterioration occurs. These include, for example, gout, osteoarthrosis, osteoarthritis, psoriasis and psoriatic arthritis, Reiter's Syndrome, systemic lupus erythmatosus and ankylosing spondylitis.

The selective beta$_2$ antagonists are known to block the beta$_2$-adrenergic receptors which are located throughout the mammalian musculoskeletal system. It has now been discovered that these agents produce potent anti inflammatory effects, probably by reducing the action of compounds which contribute to inflammation and attendant tissue deterioration. Moreover, the beta$_2$ antagonists possess high anti inflammatory activity without displaying the cardiovascular activities of the non-selective and beta$_1$-selective antagonists. This combination of attributes identifies the beta$_2$ antagonists as promising agents for treatment of a wide variety of inflammatory disease states including inflammatory bowel disease, psoriasis, chronic bronchitis, systemic lupus erythmatosus, scleroderma and the like.

Administration of the active beta$_2$ antagonists for use in the method of this invention can be via any of the accepted modes of administration for agents which control inflammation, rheumatoid arthritis and associated pain, joint and tissue degeneration. These methods include but are not limited to oral, parenteral, topical, intra-articular and otherwise systemic administration. Oral administration is preferred, depending of course, on the disorder being treated. The compounds are administered in a therapeutically effective amount either alone or in combination with a suitable pharmaceutically acceptable carrier or excipient.

Depending on the intended mode of administration, the beta$_2$ antagonist of choice may be incorporated in any pharmaceutically acceptable dosage form, such as for example, tablets, suppositories, pills, capsules, powders, liquids, suspensions, emulsions, aerosols or the like, preferably in unit dosage forms suitable for single administration of precise dosages, or sustained release dosage forms for continuous controlled administration. Preferably the dosage form will include a pharmaceutically acceptable excipient and an active beta$_2$ antagonist, and, in addition, may contain other medicinal agents, pharmaceutical agents, carriers, adjuvants, etc.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose and magnesium carbonate. An example of a solid dosage form for carrying out the invention is a suppository containing propylene glycol as the carrier. Liquid pharmaceutically administrable dosage forms can, for example, comprise a solution or suspension of an active beta2 antagonist and optional pharmaceutical adjuvants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, thriethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered will, in any event, contain a quantity of the active beta2 antagonist in an amount effective for treatment of the inflammatory disease and alleviation of the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of active beta$_2$ antagonist administered will, of course, be dependent on the subject being treated, the severity and nature of the affliction, the manner of administration, the potency and pharmacodynamics of the particular beta$_2$ antagonist and the judgment of the prescribing physician. However, the therapeutically effective dosage of the beta$_2$ antagonists for use in this invention will generally be in the range of 1–100 mg/kg/day, preferably about 1–20 mg/kg/day, and most preferably about 1 to 2 mg/kg/day. For an average 70 kg human, this would amount to 70 mg–7 g per day, or preferably 70–1400 mg or less per day.

The pharmaceutical compositions for use in the method of this invention will be formulated to contain an amount of beta$_2$ antagonist suitable for effecting the desired daily dosage range for that antagonist. Generally the amount of active beta$_2$ antagonist will be about 0.001% to about 10% of the total formulated composition.

The following Examples serve to illustrate and enable practice of the invention. They should not be construed as narrowing or limiting the scope of the invention in any way.

The effectiveness of the beta$_2$ antagonists to suppress inflammation, attenuate the progress of joint deterioration, and delay the onset of clinical symptoms of inflammatory disease was established by the tests set forth and described in detail in Examples 1 and 2, below.

EXAMPLE 1

Effect of Beta$_2$ Antagonists on Progress of Joint Deterioration

A. Procedure

The experiment was performed on 250–350 g male Sprague-Dawley rats (Bantin and Kingman, Fremont, Calif.). Arthritis was induced by intradermal injection of 0.1 ml of a 10 mg/kg suspension of *Mycobacterium butyricum* in mineral oil according to the method of Pearson et al., *Arthritis Rheum.*, 2, 440–459 (1959). The rats were bedded on soft wood shavings. Food and water were placed within easy reach inside the cages so that rats were able to eat and drink normally.

Twenty-eight days after injection of the adjuvant the rats were anesthetized and x-rayed to assess the severity of arthritis radiologically. Immediately after radiography, rats were sacrificed. A blinded observer evaluated and scored the radiographs of each hindpaw using the 0–3 grading scale of Ackerman and colleagues (*Arthritis Rheum.*, 22, 1365–1374 (1979), which assesses the following signs of joint injury: soft-tissue swelling, decreased bone density (osteoporosis), narrowing of the joint space (loss of cartilage), destruction of bone (erosions), and formation of periosteal new bone. On this scale, a score of 0 is normal and 3 designates maximum joint injury. Radiographic scores derived with this scale correlate well with scores from histological sections of arthritic joints and periarticular tissues (*Arthritis Rheum.*, 22, 1365–1374 (1979).

B. Effect of Sympatholytic Agents

The effects of various classes of sympatholytic agents on the severity of the adjuvant induced arthritic disease were determined by administering representative agents to individual groups of rats, as follows.

The effect of general sympathectomy was investigated by administering reserpine (Eli Lily Company, Indianapolis, Ind.) 0.25 mg/kg once daily. The effect of non-selective alpha-adrenergic blockade was investigated with the alpha antagonist phenoxybenzamine (Smith, Kline and French Laboratories, Philadelphia, Pa.) 30 mg/kg once daily. Non-selective beta-adrenergic blockade was assessed by administering propranolol (Ayersts Laboratories, New York, N.Y.) 20mg/kg three times daily. Selective alpha1 blockade was assessed by administering prazosin (Pfizer Inc., New York, N.Y.) 2 mg/kg five times daily. The effect of selective alpha$_2$ adrenergic blockade was investigated with the alpha$_2$ antagonist yohimbine (Sigma) 3 mg/kg once daily. The effect of selective beta$_1$ adrenergic receptor blockade was investigated by administering metoprolol (Ciba-Geigy Corporation, Summit, N.J.) 50 mg/kg three times daily). Finally, the effect of selective beta$_2$ adrenergic blockade was investigated with the selective beta$_2$ antagonists butoxamine (Burroughs Wellcome Co., Research Triangle Park, N.C.) 10, 25 or 50 mg/kg three times daily, and ICI-118,551 (Imperial Chemical Industries) 25 mg/kg three times daily. All of the sympatholytic agents were dissolved or suspended in saline and administered subcutaneously or intraperitoneally. All dosages were selected based on levels established in previously published studies with Sprague-Dawley rats. Reserpine (Sandril ®) injection USP was dissolved in 30% polythelyene glycol, 1% monoglycerol, 1% ascorbic acid and 2% benzyl alcohol. The control group of arthritic rats received injections of saline three times daily. All rats were monitored for signs of clinically apparent arthritis to determine the date of onset of clinically apparent disease. The onset of clinically apparent arthritis was defined by the first occurrence of tenderness and swelling on daily examination. Twenty-eight days after injection of the adjuvant, all rats were anesthetized, x-rayed and scored radiologically for degree of joint injury, as described in Paragraph A. The results of this test are tabulated in Tables 1 and 2, below.

C. Effect of Treatment in Different Phases of Arthritic Disease

Since the pathophysiology of adjuvant induced experimental arthritis involves physiological, immunological and clinical events that can be temporally divided into at least two distinct periods, or phases, of the disease, the effects of the previously named sympatholytic agents were also comparatively tested during the different disease phases. The first, or "pre-onset" phase is the period prior to the development of clinically apparent disease. It begins at the time of injection of mycobacterium into the tail and ends with the onset of the second, or "post-onset", phase of the disease. The latter is signaled by the abrupt appearance of tenderness and swelling. To assess the effect of each sympatholytic drug class on the course of disease in each phase, the groups of rats were further divided into three subgroups. In the first subgroup, catecholamines were depleted, or antagonists administered, starting two days prior to injecting adjuvant and continuing until day 28 after injection (pre- and post-onset), at which time all animals were examined radiologically as described in Paragraph A above. In the second subgroup catecholamines were depleted, or antagonists administered, only during the pre-onset phase of arthritis. Thus, reserpine was started 2 days prior to injection of adjuvant and continued to day 3, post-injection. Butoxamine was started 2 days prior to injection of adjuvant and continued through day 8 post-injection. This protocol allowed time for recovery of catecholamines prior to the onset of clinically apparent arthritis. In the third subgroup of rats reserpine or butoxamine was started on the day when clinically apparent arthritis was first observed (i.e. post-onset) and continued to day 28. Twenty-eight days after injection of the adjuvant, all rats were anesthetized, x-rayed and scored radiologically for degree of joint injury, as described in Paragraph A. The results of this test are tabulated in Table 3, below.

RESULTS

TABLE 1

RESULTS
Degree of joint injury in the hindlimbs of
arthritic rats administered sympatholytic drugs from
day −2 to 28

| Treatment | n(paws) | % with radiographic score | | | | Mean Score | p* |
|---|---|---|---|---|---|---|---|
| | | 0 | 1 | 2 | 3 | | |
| Saline | 24 | 8.5 | 25.0 | 37.5 | 29.0 | 1.9 ± 0.2 | |
| Reserpine | 12 | 66.0 | 17.0 | 17.0 | 0.0 | 0.5 ± 0.2 | <0.0 |
| Phenoxybenzamine | 6 | 0.0 | 0.0 | 50.0 | 50.0 | 2.5 ± 0.2 | NS |
| Prazosin | 12 | 17.0 | 49.0 | 17.0 | 17.0 | 1.3 ± 0.3 | NS |
| Yohimbine | 12 | 17.0 | 17.0 | 58.0 | 0.0 | 1.5 ± 0.3 | NS |
| Propranalol | 18 | 61.0 | 39.0 | 0.0 | 0.0 | 0.4 ± 0.1 | <0.0 |
| Metoprolol | 12 | 16.0 | 0.0 | 42.0 | 42.0 | 2.0 ± 0.3 | NS |
| Butoxamine** | 14 | 57.0 | 43.0 | 0.0 | 0.0 | 0.4 ± 0.1 | <0.0 |
| ICI 118,551 | 12 | 67.0 | 33.0 | 0.0 | 0.0 | 0.3 ± 0.1 | <0.0 |

*Comparisons with saline (control) group based on $x^2$ or Fisher's exact test on a 2 × 2 table produced by combining the frequencies of 0 and 1 scores and of 2 and 3 scores. NS, not significant.
**Dose, 25 mg/kg daily. All other doses were as set forth in Paragraph B, above.

TABLE 2

| Delay in Onset of Clinically Apparent Arthritis | | | |
|---|---|---|---|
| Treatment | n (paws) | Day of Onset* | p** |
| saline | 24 | 13.5 ± 1.5 days | |
| Reserpine | 12 | 21.8 ± 3.0 days | <0.01 |
| Phenoxybenzamine | 6 | 13.0 ± 2.1 days | >0.05 |
| Prazosin | 12 | 16.2 ± 2.9 days | NS |
| Yohimbine | 12 | 13.6 ± 0.6 days | NS |
| Propranalol | 18 | 19.8 ± 1.7 days | <0.05 |
| Metoprolol | 12 | 14.0 ± 1.8 days | NS |
| Butoxamine*** | 14 | 22.9 ± 1.9 days | <0.01 |
| ICI 118,551 | 12 | 20.0 + 3.0 days | <0.05 |

*Number of days after injection of adjuvant until onset of clinically apparent arthritic disease.
**Fisher's exact test.
***Dose, 25 mg/kg daily. All other doses were as set forth in Paragraph B, above.

TABLE 3

Comparison of effects of sympathectomy (reserpine) and Beta$_2$ blockade (butoxamine) administered (i) pre- and post onset (day −2 to 28), (ii) pre-onset (reserpine days −2 to 3 or butoxamine days −2 to 8), or (iii) post-onset (first day of clinical arthritic symptoms to day 28).

| Treatment | n | Mean Score | P |
|---|---|---|---|
| Pre- and Post Onset | | | |
| Reserpine | 12 | 0.50 ± 0.23 | <0.01 |
| Butoxamine | 14 | 0.43 ± 0.14 | <0.01 |
| Pre-Onset | | | |
| Reserpine | 12 | 0.75 ± 0.25 | <0.01 |
| Butoxamine | 14 | 1.00 ± 0.20 | <0.01 |
| Post-Onset | | | |
| Reserpine | 12 | 1.04 ± 0.16 | <0.01 |
| Butoxamine | 14 | 1.31 ± 0.33 | <0.05 |

D. Discussion of Results

The test results set forth in Table 1 establish that it is beta2-selective adrenergic blockade which reduces inflammation and attenuates the progress of joint injury in arthritic disease. The non-selective alpha$_2$ antagonist phenoxybenzamine, the selective alpha$_1$ and alpha$_2$ antagonists prazosin and yohimbine, and the selective beta$_1$ antagonist metoprolol, did not significantly affect the severity of joint injury in comparison with the controls. In contrast, the total sympathetic blocker, reserpine, the non-selective beta blocker, propranolol and the selective beta$_2$ antagonists, butoxamine and ICI 118,551, markedly attenuated the severity of joint injury. The fact that butoxamine and ICI 118,551 were equally effective as reserpine and propranolol, whereas the beta1 antagonist metoprolol was ineffective indicate that the therapeutic effect of the non-specific beta-adrenergic antagonist was mediated by its blockade of beta$_2$-rather than beta1-adrenergic receptors.

The test results set forth in Table 2 establish that administration of the beta2-antagonists butoxamine or ICI 118,551 significantly delays the onset of clinically apparent arthritic disease. In contrast, animals treated with prazosin, yohimbine or metoprolol had onset latencies which did not differ from the saline treated controls.

The test results set forth in Table 3 establish that when sympathetic activity is reduced with either reserpine (depletion) or butoxamine (beta$_2$ blockade), a highly significant attenuation of joint injury was effected even when treatment began after onset of clinical symptoms of disease. Thus, the inflammatory events mediated through the beta$_2$-adrenergic receptor influence both the onset (initiation) and progression of the joint injury in arthritis.

EXAMPLE 2

Dose Response Effects of Butoxamine

Experimental arthritis was induced in rats as described in Example 1, Paragraph A, above. Butoxamine was administered at a dose of 10, 25 or 50 mg/kg daily either from day −2, or from the first day that clinical arthritis was detected, to day 28. An untreated control group received only saline. At day 28, all rats were anesthetized, sacrificed, and the severity of arthritis examined radiologically as described in Example 1, Paragraph A. Table 4 gives the resulting radiographic scores.

TABLE 4

Dose Response Effects of Butoxamine

| dose (mg/kg/day) | Mean Radiographic Score | P |
|---|---|---|
| Untreated control | 1.78 ± 0.24 | |
| Pre- and Post Onset | | |
| 10 | 1.08 ± 0.25 | <0.05 |
| 25 | 0.43 ± 0.14 | <0.01 |
| Post Onset | | |
| 10 | 1.33 ± 0.38 | NS |
| 25 | 1.31 ± 0.33 | NS |
| 50 | 0.67 ± 0.13 | <0.01 |

I claim:

1. A method of treating inflammatory disorders in mammals which comprises administering a therapeutically effective amount of a selective beta$_2$ antagonist to a mammal in need of such treatment, wherein the antagonist is an alkylaminoalkanol selected from the group consisting of butoxamine, ICI 118,551 and H35/25.

2. A method of claim 1 in which the beta$_2$ antagonist has a beta$_2$/beta$_1$ selectivity ratio of at least 10.

3. A method of claim 2 in which the beta$_2$ antagonist has a beta$_2$/beta$_1$ selectivity ratio of at least 50.

4. The method of claim 1 in which the disorder is rheumatoid arthritis.

5. A method of claim 4 in which the beta$_2$ antagonist has a beta$_2$/beta$_1$ selectivity ratio of at least 10.

6. A method of claim 5 in which the beta$_2$ antagonist has a beta$_2$/beta$_1$ selectivity ratio of at least 50.

7. A method of claim 1 in which the disorder is osteoarthritis.

8. A method of claim 1 in which the disorder is psoriasis.

9. A method of claim 1 in which the disorder is inflammatory bowel disease.

10. A method of claim 1 in which the beta$_2$ antagonist is selected from the group consisting of D,L-erythro-α-(2,5-dimethoxyphenyl)-β-t-butylaminopropanol hydrochloride, erythro-D,L-1-(methylinden-4-yloxy)-3-isopropylaminobutan-2-ol, and 1-(4'-methylphenyl)-2,2-isopropylaminopropanol.

11. A method of claim 1 in which the disorder is characterized by joint deterioration.

12. A method of claim 6 in which the disorder is degenerative joint disease.

13. A method of treating disorders in mammals characterized by the presence of progressive joint deterioration, which method comprises administering a therapeutically effective amount of a selective beta$_2$ antagonist to a mammal in need of such treatment, wherein the antagonist is an alkylaminoalkanol selected from the group consisting of butoxamine, ICI 118,551 and H35/25.

14. A method of claim 13 in which the beta$_2$ antagonist has a beta$_2$/beta$_1$ selectivity ratio of at least 10.

15. A method of claim 14 in which the beta$_2$ antagonist has a beta$_2$/beta$_1$ selectivity ratio of at least 50.

16. A method of claim 13 in which the disorder is rheumatoid arthritis.

17. A method of claim 14 in which the disorder is rheumatoid arthritis.

18. A method of claim 15 in which the disorder is rheumatoid arthritis.

19. The method of claim 13 in which the disorder is degenerative joint disease.

20. A method of treating a disorder in a mammal characterized by the presence of progressive tissue deterioration, which method comprises administering an effective amount of a selective beta$_2$ antagonist to a mammal in need of such treatment, wherein the antagonist is an alkylaminoalkanol selected from the group consisting of butoxamine, ICI 118,551 and H35/25.

21. A method of claim 20 in which the disorder is systemic lupus erythmatosus.

22. A method of claim 13 in which the beta$_2$ antagonist is selected from the group consisting of D,L-erythro-α-(2,5-dimethoxyphenyl)-β-t-butylaminopropanol hydrochloride, erythro-D,L-1-(methylinden-4-yloxy)-3-isopropylaminobutan-2-ol, and 1-(4'-methylpenyl)-2,2-isopropylaminopropanol.

23. A method of claim 20 in which the beta$_2$ antagonist is selected from the group consisting of D,L-erythro-α-(2,5-dimethoxyphenyl)-β-t-butylaminopropanol hydrochloride, erythro-D,L-1-(methylinden-4-yloxy)-3-isopropylaminobutan-2-ol, and 1-(4'-methylphenyl)-2,2-isopropylaminopropanol.

* * * * *